United States Patent [19]

Greco

[11] 3,933,925
[45] Jan. 20, 1976

[54] HYDROLYSIS OF TOLUENE DIAMINES TO PRODUCE METHYL RESORCINOLS

[75] Inventor: Nicholas P. Greco, Edgewood, Pa.

[73] Assignee: Koppers Company, Inc., Pittsburgh, Pa.

[22] Filed: Jan. 17, 1975

[21] Appl. No.: 542,087

Related U.S. Application Data

[63] Continuation-in-part of Ser. No. 267,525, June 29, 1972, Pat. No. 3,862,247, which is a continuation-in-part of Ser. No. 16,545, March 4, 1970, abandoned.

[52] U.S. Cl............ 260/621 M; 423/520; 260/625
[51] Int. Cl.² ........................................ C07C 39/08
[58] Field of Search..... 260/621 M, 621 H, 16, 545, 260/267, 525, 625; 423/520

[56] References Cited
UNITED STATES PATENTS 2,665,313   1/1954   Lisk................ 260/621 M Primary Examiner—James O. Thomas, Jr.
Assistant Examiner—W. B. Lone
Attorney, Agent, or Firm—Oscar B. Brumback; Herbert J. Zeh, Jr.

[57] ABSTRACT

Methyl resorcinols are produced by the hydrolysis of toluene diamines in an aqueous excess of ammonium bisulfate. The reactants are contacted at an elevated temperature for a period of time sufficient to hydrolyze the toluene diamines to methyl resorcinols. The methyl resorcinols so produced are separated from the reaction mixture. The ammonium sulfate is regenerated to ammonium bisulfate by removing the water and thermally decomposing the by-product ammonium sulfate at an elevated temperature.

7 Claims, No Drawings

HYDROLYSIS OF TOLUENE DIAMINES TO PRODUCE METHYL RESORCINOLS

CROSS REFERENCE TO RELATED APPLICATIONS

This application is a continuation-in-part of my copending application Ser. No. 267,525 filed June 29, 1972 now U.S. Pat. No. 3,862,247 which, in turn, is a continuation-in-part of application Ser. No. 16,545 filed Mar. 4, 1970 now abandoned.

BACKGROUND OF THE INVENTION

This invention relates to the production of methyl resorcinol and more particularly to the hydrolysis of toluene diamines with ammonium bisulfate to produce methyl resorcinols.

Methyl resorcinols have mild germicidal and antiseptic properties and consequently find use in skin lotions and hair tonics.

Toluene is readily nitrated to the dinitro stage. This stage is reached as a mixture of two isomers 2,4-dinitrotoluene and 2,6-dinitrotoluene. The predominate isomer is the 2,4-dinitrotoluene. These isomers can be readily reduced to the corresponding amines. The amine isomers can be separated, for example, by distillation and are commercially available. While the separate isomers can be used in the practice of this invention, it has been found that for many uses of the methyl resorcinols, it is not necessary to separate the isomers but the mixture of amines may be used to obtain a mixture of methyl resorcinol isomers.

SUMMARY OF THE INVENTION

In accordance with this invention, methyl resorcinol is made by the ammonium bisulfate hydrolysis of toluene diamine by contacting the toluene diamine with at least 4 but preferably 6 moles of ammonium bisulfate per mole of toluene diamine in aqueous solution at a temperature of about 200° to 300°C., preferably 220°C., for a time sufficient to hydrolyze the toluenediamine to methyl resorcinol. The aqueous solution is then cooled and the product methyl resorcinol extracted using a suitable organic inert solvent. The reaction may be expressed as

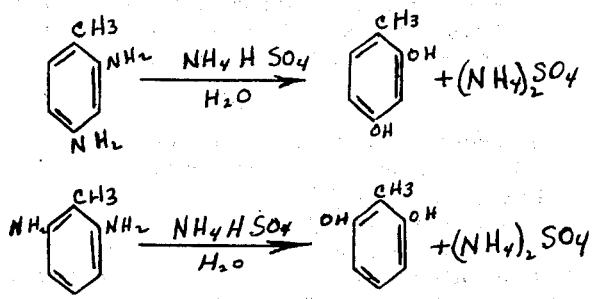

Hydrolysis may be repeated by reheating the reaction mixture after extraction, or the ammonium sulfate can be regenerated for reuse in the reaction by evaporating the water and heating the melt of the mixed ammonium sulfates at a temperature of 310° to 450°C. Upon cooling the resulting ammonium bisulfate is dissolved in water, adjusted to the desired concentration and recycled to the reaction zone. The solvent solution from the extraction step is evaporated to give substantially pure methyl resorcinol.

DETAILED DESCRIPTION

In accordance with this invention, toluene diamine is hydrolyzed in an aqueous medium through the use of ammonium bisulfate to produce methyl resorcinol. The by-product salt can be regenerated to ammonium bisulfate for reuse in the process.

The composition of the hydrolysis medium is of particular importance. A minimum of 4 but preferably 6 moles of ammonium bisulfate based on the number of moles of toluene diamine is necessary in order to provide a reasonable yield of methyl resorcinol in a single hydrolysis reaction. The hydrolysis can be carried out in one step or it can be continued sequentially by terminating the reaction, cooling, extracting the product and reheating the hydrolysis mixture without further addition of reactants. A one-step hydrolysis is desirable from the standpoint of ease and efficiency of operation, although an increase in yield can be achieved by a second hydrolysis of the reaction mixture after removing the product from the first hydrolysis. From the standpoint of obtaining high yields in a single hydrolysis step, the use of high concentrations of ammonium bisulfate up to the point of saturation of the aqueous solution is desirable. With high concentrations, a practical problem arises in the handling of large quantities of salt.

Water must be present in an amount sufficient to provide for hydrolysis and also to serve as a diluent or solvent for the toluene diamine ammonium bisulfate and the methyl resorcinol and ammonium sulfate formed during the course of the reaction. At least 40, but preferably 60, moles of water per mole of toluene diamine must be present to dissolve sufficient quantities of ammonium bisulfate. As the concentration of ammonium bisulfate is increased, more water, up to about 120 moles, is required. The use of excess water results in a practical problem of water removal during the ammonium bisulfate regeneration step.

The reaction temperature can vary over a wide range between about 200° to 300°C. At temperatures below about 200°C. an unduly long reaction time is required and the yields are generally low. As the temperature is increased the pressure must be correspondingly increased to maintain the reaction medium in the aqueous phase. At temperatures as high as 300°C. a steam pressure of up to about 1500 psig is required for this purpose and there is some danger of resin formation if the contact time is too long. No advantage is obtained by increasing or decreasing the pressure to a value other than that sufficient to provide for a liquid reaction medium. To avoid the use of considerable pressure, with the corresponding equipment requirements, temperatures in the range of 220° to 260°C. are preferred.

The reaction time or contact time varies primarily with the temperature and to a lesser extent with the mole ratio of the reactants. At a minimum temperature, e.g., 200°C., a per pass reaction time of 8 hours is ordinarily required. At 220°C. effective results from the standpoint of yield are obtained using a two pass hydrolysis reaction and a reaction time of 5 hours per pass. Also at 220°C. good results are obtained in a single pass hydrolysis step if the reaction time is extended to 7 or 8 hours. At temperatures about 250°C., hydrolysis can occur in 5 minutes to a half hour. From a practical standpoint an overall per pass hydrolysis time can be considered to be from 5 minutes to 8 hours.

Hydrolysis is carried out in a zone which is resistant to any substantial attack by the ammonium bisulfate or toluene diamine. At very low temperatures within the useful range an ordinary glass lined Pfaudler kettle can be used. When higher temperatures are required, other construction materials become necessary. At temperatures up to 220°–230°C. Teflon lined reactors are effective. Higher temperature ranges require the use of more durable equipment, such as tantalum lined reactors.

After the period of hydrolysis, the reaction mixture is cooled to prevent resinification of the product in the acidic aqueous reaction mixture and to enable the separation of the by-product of organic solvent extraction. Any substantially water-immiscible solvent which will dissolve the methyl resorcinol is useful. Ethyl ether is the preferred solvent.

The organic solvent phase is then separated from the reaction mixture by decantation and the product is removed from the solvent by distillation or evaporation of the solvent.

After removal of the methyl resorcinol product, the remaining aqueous reaction mixture can be reheated to the hydrolysis temperature for a second or even a third hydrolysis step. The second and subsequent hydrolysis steps are carried out as before by heating the reaction mixture to the appropriate temperature of hydrolysis for the desired period of time, cooling and removing the product resorcinol by solvent extraction.

Ammonium sulfate by-product is regenerated for reuse in the process by removing the residual water from the remaining reaction mixture and heating the molten salt, primarily mixed ammonium sulfate, and ammonium bisulfate at atmospheric pressure at a temperature between 310° to 450° C. At temperatures below 310°C. an unduly long time is required to effect decomposition. No practical advantages are seen in using temperatures higher than 450° C. and above this temperature the bisulfate tends to decompose. At 330° C., 75 to 95 percent of the ammonium sulfate is converted in a few minutes to ammonium bisulfate. Slightly higher conversions are obtained at higher temperatures although this advantage is offset by the increased equipment cost required. During the decomposition of the ammonium sulfate, residual organic materials may be pyrolyzed to black granules resembling activated charcoal. This charcoal-like material is easily removed by dissolving the product in water followed by a filtration step. The ammonia formed during the decomposition can be recovered and used in other chemical processes. The clear, filtered salt solution, the salt portion of which 75 to 95 percent ammonium bisulfate, is adjusted to the desired concentration and is recycled to the reaction mixture for hydrolysis of additional toluene diamine.

My invention is further illustrated by the following examples.

EXAMPLE I

A commercially available mixture of toluene diamine isomers was hydrolyzed to methyl resorcinol using ammonium bisulfate. To this end, a reactor was charged with toluene diamine (24.2 g, 0.2 mole) analyzing 20% of the 2,6 diamino toluene isomer and 80% of the 2,4 diamino toluene isomer, ammonium bisulfate (138 g., 1.2 moles) and water (216 g., 12 moles) was heated to 220° C. for 5 hours. The amber colored reaction mixture was cooled and was shaken with ethyl ether twice for two extractions (2 × 200 ml). The aqueous solution after boiling to remove dissolved ether was heated again for 5 more hours at 220°C. The reaction mixture was cooled and was extracted with ether in two extractions (2 × 200 ml). The ether solutions were stripped to dryness on a steam bath leaving the nearly white solid of mixed methyl resorcinol isomers. The first ether extract gave 16.0 g. of methyl resorcinol and the second ether extract gave 3.6 g. of methyl resorcinol for a total yield of 81.4 percent. The mixture was purified by strip distillation through a 30 inch by ⅝ inch stainless steel cannon packed column (bp 139° C. at 5 min.). The distillate was subjected to V.P.C. analysis and was found to be a mixture of 19 percent of the 2-methyl resorcinol and 81 percent of the 4-methyl resorcinol.

The aqueous reaction medium remaining after the ether extraction was decomposed to provide bisulfate for recycling. The inorganic sulfates present after evaporating the effluent to a dry salt then was heated in an oil bath and could be stirred easily after reaching 146° C. which is the melting point of ammonium bisulfate. Heating was continued until a temperature of 312° C. was reached and the melt was held at 312° C. for about 15 minutes. Any organic material in the effluent was converted to fine carbonaceous particles during the heating of the melt. The thermally treated salt mixture was taken up in water and the black mixture filtered. After filtering, the ammonium bisulfate solution was clear. Evaporation of the filtrate gave light yellow ammonium bisulfate crystals for reuse in further hydrolysis.

EXAMPLE II

The reactor was charged with the following:
24.2 g. (0.2 m) 2,4-toluenediamine
216 g. $H_2O$ (12.0 m)
138 g. $NH_4HSO_4$ (1.2 m) The charge was heated at 220° C. for 6 to 7 hours for the hydrolysis. The product was filtered and the filtrate extracted twice with 200 ml each of ethyl ether. Evaporation of the ether to dryness gave 17.1 g. (69 percent) of nearly white 4-methyl resorcinol. The aqueous phase remaining after the ether extraction was subjected to a second hydrolysis treatment like the first and gave 3.3 g. more of methyl resorcinol for a total of 20.4 g. a 82.5% yield of 4-methyl resorcinol (99+ percent purity by gas chromatography).

EXAMPLE III

The following was charged to a reactor:
24.2 g. of (0.2 m.) 2,6 toluenediamine
216 g. (12.0 m.) of $H_2O$
138 g. (1.2 m.) of $NH_4HSO_4$
The solution was heated at 220°C. for 5 hours for the hydrolysis reaction. Then the reaction mixture was filtered to remove a small amount of tar. The filtrate extracted twice with 200 ml of ethyl ether each time and the ether evaporated to dryness to give 15 g. of nearly white solid of 2-methyl resorcinol. The aqueous phase remaining after the ether extraction was again heated in the reactor for further hydrolysis for 5 hours more and the methyl resorcinol removed by ether extraction in the same manner as the first hydrolysis to give 4.1 g. more of 2-methyl resorcinol. The total yield on two passes at hydrolysis was 77 percent. Analysis by gas chromatography showed it to be 99+ percent pure.

The foregoing has provided a convenient process for the production of methyl resorcinol.

What is claimed is:

1. A method of making methyl resorcinol comprising:
   a. contacting toluene diamine with ammomium bisulfate in an aqueous solution that contains 4 to 12 moles of ammonium bisulfate per mole of toluene diamine and 40 to 120 moles of water per mole of toluene diamine and that is at a temperature of 200° to 300° C. for a period of one-half to eight hours to hydrolyze said toluene diamine to methyl resorcinol,
   b. cooling said hydrolysis reaction mixture, and
   c. extracting said methyl resorcinol from said solution with a water-immiscible organic solvent.

2. The method of claim 1 wherein the solution from which the methyl resorcinol has been extracted is maintained at a temperature of 200° to 260° C. for an additional period of time to hydrolyze residual of said toluene diamine to methyl resorcinol.

3. The method of making methyl resorcinol comprising:
   a. contacting toluene diamine with ammonium bisulfate in an aqueous solution that contains 4 to 12 moles of ammonium bisulfate per mole of toluene diamine and 40 to 120 moles of water per mole of toluene diamine and that is at a temperature of 200° to 260° C. for a period of one-half to eight hours to hydrolyze said toluene diamine to methyl resorcinol.
   b. cooling said hydrolysis reaction mixture,
   c. extracting said methyl resorcinol from said solution with an inert water-immiscible organic solvent, thereafter
   d. evaporating the water from said solution to obtain a residue consisting essentially of ammonium sulfate and ammonium bisulfate, and
   e. heating said residue to an elevated temperature of 210 to 450° C. to convert said ammonium sulfate to ammonium bisulfate for reuse to hydrolyze more toluene diamine to methyl resorcinol.

4. A method of making 4-methyl resorcinol comprising:
   a. contacting 2,4-toluene diamine with ammonium bisulfate in an aqueous solution that contains 4 to 12 moles of ammonium bisulfate per mole of 2,4-toluene diamine and 40 to 120 moles of water per mole of 2,4-toluene diamine and that is at a temperature of 200° to 300° C. for a period of one-half to eight hours to hydrolyze said 2,4-toluene diamine to 4-methyl resorcinol,
   b. cooling said hydrolysis reaction mixture, and
   c. extracting said 4-methyl resorcinol from said solution with a water-immiscible organic solvent.

5. The method of claim 4 wherein the solution from which the 4-methyl resorcinol has been extracted is maintained at a temperature of 200° to 260° C. for an additional period of time to hydrolyze residual of said toluene diamine to 4-methyl resorcinol.

6. A method of making 2-methyl resorcinol comprising:
   a. contacting 2,6 toluene diamine with ammonium bisulfate in an aqueous solution that contains 4 to 12 moles of ammonium bisulfate per mole of toluene diamine and 40 to 120 moles of water per mole of toluene diamine and that is at a temperature of 200° to 300° C. for a period of one-half to eight hours to hydrolyze said 2,6-toluene diamine to 2-methyl resorcinol,
   b. cooling said hydrolysis reaction mixture, and
   c. extracting said 2-methyl resorcinol from said solution with a water-immiscible organic solvent.

7. The method of claim 6 wherein the solution from which the 2-methyl resorcinol has been extracted is maintained at a temperature of 200° to 260° C. for an additional period of time to hydrolyze residual of said toluene diamine to 2-methyl resorcinol.

* * * * *